(12) United States Patent
Karpf et al.

(10) Patent No.: US 6,562,977 B2
(45) Date of Patent: May 13, 2003

(54) PROCESS FOR THE PREPARATION OF MIXED ANHYDRIDES

(75) Inventors: Martin Karpf, Reinach (CH); René Trussardi, Birsfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/008,981

(22) Filed: Dec. 6, 2001

(65) Prior Publication Data

US 2002/0077481 A1 Jun. 20, 2002

Related U.S. Application Data

(62) Division of application No. 09/359,294, filed on Jul. 22, 1999, which is a continuation of application No. 08/976,800, filed on Nov. 24, 1997, now abandoned.

(30) Foreign Application Priority Data

Dec. 11, 1996 (EP) .............................................. 96119853

(51) Int. Cl.$^7$ ...................... C07D 215/12; C07D 215/20

(52) U.S. Cl. .......................... 546/170; 546/167; 546/168

(58) Field of Search ................................ 546/167, 168, 546/170

(56) References Cited

U.S. PATENT DOCUMENTS

| | | |
|---|---|---|
| 4,764,617 A | 8/1988 | Masaki et al. |
| 4,874,558 A | 10/1989 | Fife et al. |
| 5,157,041 A | 10/1992 | Handa et al. |
| 5,196,438 A | 3/1993 | Martin et al. |
| 5,455,353 A | 10/1995 | Hilpert |
| 5,502,210 A | 3/1996 | Hilpert |
| 5,523,463 A | 6/1996 | Hilpert |
| 5,536,816 A | 7/1996 | Hohler et al. |
| 5,591,885 A | 1/1997 | Hilpert |

FOREIGN PATENT DOCUMENTS

| | | |
|---|---|---|
| EP | 256 181 | 2/1988 |
| ZA | 86 0 6196 | 4/1987 |

OTHER PUBLICATIONS

Masaki, CA 108:186589, abstract, 1987.*
M. Bodansky: "Principles of Peptide Synthesis", 2nd ed. Springer–Verlag, Berlin, pp. 21–29 (1993).
M. Bodansky: The Practice of Peptide Synthesis, 2nd ed., Springer Verlag, Berlin, pp. 89–95 (1994).
Alig, et al., Low Molecular Weight, Non–Peptide Fibrinogen Receptor Antagonists, J. Med. Chem. vol. 35, pp. 4393–4407 (1992).
Weller, et al, Orally Active Fibrinogen Receptor Antagonists. 2. Amidoximes as Prodrugs of Amidines, J. Med. Chem vol. 39, pp. 3139–3147 (1996).

Reitz, et al., $N^1$–Sterically Hindered 2H–Imidazol–2–One Angiotensin II Receptor Antagonists: The Synthesis of [$^3$H]–SC–54628 And [$^3$H]SC–54629, Bioorganic & Medicinal Chemistry Letters, vol. 4, No. 1, pp. 111–114 (1994).
Chemical Abstract No. 186589a, vol. 198, No. 21, May 23, 1988.
Chemical Abstract No. 323378v, vol. 120, No. 25, Jun. 20, 1994.
Chemical Abstract No. 6451f, vol. 105, No. 1, Jul. 7, 1986. UKR, Khim, ZH, vol. 51, No. 8, pp. 860–865 (1985).
Chemical Abstract 123:199359, Moree, et al., Synthesis of Peptidosulfinamides and Peptidosulfonamides: Peptidomimetics Containing the Sulfinamide or Sulfonamide Transition–State Isostere, J. Org. Chem. vol. 60, pp. 5157–5169 (1995).
Chemical Abstracts 121: 157574, Langry, Synthesis of Imidazoquinolines and Imidazoquinolines from Azanapthalene Carboxylic Acids, Organic Preparations and Procedures Int., vol. 26, pp. 429–438 (1994).
Chemical Abstracts 115:256588, Kerwin, et al., Cholecystokinin Antagonists: (R)–Tryptophan–Based Hybrid Antagonists of High Affinity and Selectivity for CCK–A Receptors, J. Med. Chem., vol. 34, pp. 3350–3359, (1991).
Chemical Abstracts 114:122306, Sashida, et al., Studies of Seven–Membered Heterocycles, XXXII. Synthesis of N–Unsubstituted 1H–1,4–Benzodiazepines Stabilized by Intramolecular Hydrogen Bonding, Chem. Pharm. Bull, vol. 38, No. 11, pp. 2919–2925 (1990).
Chemical Abstracts 109:210867, Shrader, et al., Synthesis of a Novel Hexadentate Chelating Agent Based on 8–Hydroxy–quinoline, Tetrahedron Letters, vol. 29, No. 12, pp. 1351–1354 (1988).
Chemical Abstracts 109:170845, Shinkai, et al., N–Acylphenylalanine and Related Compounds. A New Class of Oral Hypoglycemic Agents, J. Med. Chem. vol. 31, pp. 2092–2097 (1988).
Chemical Abstracts 106:119513, Rao, et al., Synthesis of Lavendamycin, Tetrahedron, vol. 42, No. 18, pp. 5065–5071, (1986).
Chemical Abstracts 108:186589, Masaki, abstract of ZA 8606196, 1987.
Chem. Pharm. Bull, 24(5), pp. 852–858 (1976).
Justus Liebigs Ann. Chem. 1937, vol. 530, p. 34–45.
Helv. Chim. Acta. 1994. 1994, vol. 77 pp. 575–578.
Tetrahedron, 1984, vol. 40, pp. 4415–4424.
Corresponding to C19: Krollpfeiffer, F., et al., Organic Chemistry, vol. 31 pp. 5361–5364 (1937).

(List continued on next page.)

Primary Examiner—D. Margaret Seaman
(74) Attorney, Agent, or Firm—George W. Johnston; Patricia S. Rocha-Tramaloni; Bernard Lau

(57) ABSTRACT

The present invention is concerned with mixed anhydrides. The mixed anhydrides are prepared by adding an adjuvant base to a mixture of acid and reactive acid derivative. The mixed anhydrides play an role primarily in activating and coupling reactions.

2 Claims, No Drawings

OTHER PUBLICATIONS

Moree et al., J. Org. Chem., vol. 60, pp. 5157–5169 (1995).
Kevin C. Langry, Organic Preparations and Procedures Int., vol. 26, pp. 429–438 (1994).
Kerwin et al., J. Med. Chem., vol. 34, pp. 3350–3359 (1991).
Sashida et al., Chem. Pharm. Bull., vol. 38(11), pp. 2919–2925 (1990).
Shrader et al., Tetrahedron Letter, vol. 29, No. 12, pp. 1351–1354 (1988).
Rao et al., Tetrahedron, vol. 42, No. 18, pp. 5056–5071 (1986).
Shinkai et al., J. Med. Chem., vol. 31, pp. 2092–2097 (1988).

* cited by examiner

PROCESS FOR THE PREPARATION OF MIXED ANHYDRIDES

This application is a divisional of Ser. No. 09/359,294, filed Jul. 22, 1999, which is a continuation of Ser. No. 08/976,800, filed Nov. 24, 1997, now abandoned.

FIELD OF THE INVENTION

The present invention is in the field of the manufacture of mixed anhydrides.

BACKGROUND OF THE INVENTION

The manufacture of mixed anhydrides is known per se and is based on the reaction of an acid with a reactive acid derivative, for example an acid halide or acid anhydride in the presence of an adjuvant base. The production of mixed anhydrides has been described, for example, by Bodansky in "Principles of Peptide Synthesis", 2nd ed., published by Springer Berlin, 1993, pages 21–29 and in "The Practice of Peptide Synthesis", 2nd ed., published by Springer, Berlin, 1994 as well as by Stelzel in Houben-Weyl, volume XV/2, "Methoden der organischen Chemie: "Synthese von Peptiden", part II.

Mixed anhydrides play a role primarily in activating and coupling reactions. Thus, Bodansky (loc.cit.) describes the synthesis of mixed anhydrides with pivaloyl chloride for use in the synthesis of peptides. For example, for the production of benzyloxycarbonyl-$\alpha$-methylalanyl-$\alpha$-methylalanine methyl ester, acid and adjuvant base are provided and the acid chloride is added. The mixture is stirred at –5° C. for 2 hours and subsequently at room temperature for 1 hour. The production of benzyloxycarbonyl-$N^\epsilon$-$\alpha$-p-toluenesulphonyl-L-lysylglycine ethyl ester proceeds analogously.

Stelzel (loc. cit.) describes the synthesis of N-benzyloxycarbonyl-L-prolyl-L-leucylglycine ethyl ester based on the addition of isovaleroyl chloride to a mixture of Z-Pro-OH and triethylamine in toluene.

However, these and other known processes for the production of mixed anhydrides have considerable disadvantages. Thus, the reaction does not proceed quantitatively by a long way. This is primarily due to the formation of byproducts, e.g. by disproportionation to the corresponding symmetrical anhydrides. Consequently, it is necessary to subject the reaction mixture to a costly working-up and purification.

SUMMARY OF THE INVENTION

This invention provides a process for producing an anhydride of two different carboxylic acids, comprising forming a mixture of a first carboxylic acid and a reactive acid derivative of a second carboxylic acid other than the first carboxylic acid, and reacting said mixture in the presence of a base to produce said anhydride, said base being added to said mixture to initiate the reaction.

By first mixing a carboxylic acid and the reactive acid derivative of a different carboxylic acid, and only afterwards combining the mixture with the base, it has surprisingly been found that the formation of unwanted byproducts including the symmetrical anhydrides can be largely avoided. Consequently, the yield of the desired mixed anhydride is increased. Because of the increased yield this invention provides a more efficient reaction for producing mixed anhydrides. Additionally, the production of mixed anhydrides is rendered more economical since the reaction product is more pure and therefore requires less post-reaction purification.

DETAILED DESCRIPTION OF THE INVENTION

This invention provides a process for producing an anhydride of two different carboxylic acids, comprising forming a mixture of a first carboxylic acid and a reactive acid derivative of a second carboxylic acid other than the first carboxylic acid, and reacting said mixture in the presence of a base to produce said anhydride, said base being added to said mixture to initiate the reaction.

In accordance with this invention any of the conventional conditions for forming an anhydride by reacting a carboxylic acid, a reactive acid derivative, and a base, can be used. What is important is that the base is not added until a mixture of the first carboxylic acid and the reactive acid derivative is formed.

Preferably the first carboxylic acid and the reactive acid derivative are present in the mixture in a molar ratio of about 1:1, however either the first carboxylic acid or the reactive acid derivative can be present in excess. Preferably the base is present in the mixture in an amount which is at least about one mole per mole of the first carboxylic acid. More preferably, the base is present in an amount which is from about one mole to about two moles per mole of the first carboxylic acid. Still more preferably the base is present in an amount which is about one mole per mole of the first carboxylic acid. Preferably the base is present in the mixture in an amount which is at least about one mole per mole of the reactive acid derivative. More preferably, the base is present in an amount which is from about one mole to about two moles per mole of the reactive acid derivative. Still more preferably, the base is present in an amount which is about one mole per mole of the reactive acid derivative.

This reaction is generally applicable and can be used for making any mixed anhydride. The first carboxylic acid and the second carboxylic acid can be any carboxylic acid provided that they are different from each other. The term "carboxylic acid" means any compound having a —COOH moiety. These can be e.g. unsubstituted and substituted aliphatic, aromatic, aromatic-aliphatic, heteroaromatic or heteroaromatic-aliphatic carboxylic acids or protected aminocarboxylic acids, e.g. N-acylated aminocarboxylic acids such as natural N-acylated $\alpha$-amino acids having the L-configuration or corresponding non-natural N-acylated $\alpha$-amino acids having the D-configuration as well as the corresponding racemates of the L- and D-amino acids. Moreover, homologues of such amino acids can be used, e.g. amino acids in which the amino acid side-chain is lengthened or shortened by one or two methylene groups and/or in which a methyl group is replaced by hydrogen. Furthermore, there can be used substituted aromatic N-acylated $\alpha$-amino acids, e.g. substituted phenylanine or phenylglycine, which can carry one or more of the following substituents—independently of one another—: alkyl, e.g. methyl, halogen, a protected hydroxy group, alkoxy, e.g. methoxy, alkanoyloxy, e.g. acetoxy, a protected amino or alkylamino group, alkyanoylamino, e.g. acetylamino or pivaloylamino, alkoxycarbonylamino, e.g. t-butoxycarbonylamino, arylmethoxycarbonylamino, e.g. benzyloxycarbonylamino or 9-fluorenylmethoxycarbonyl, and/or nitro. Moreover, benz-fused phenylalanine or phenylglycine, such as α-naphthylamine, or hydrogenated phenylalanine or phenyglycine, such as cyclohexylalanine or cyclohexylglycine, a 5- or 6-membered cyclic benz-fused N-acylated α-amino acid, e.g. indoline-2-carboxylic acid or 1,2,3,4-tetrahydroisoquinoline-3-carboxylic acid, also come into consideration. Furthermore, natural or homologous N-acylated α-amino acids in which a carboxy group in the side-chain is present in a esterified or amidated form, e.g. as an alkyl ester group, such as methoxycarbonyl or t-butoxycarbonyl, or as a carbamoyl group, an alkylcarbamoyl group, such as methylcarbamoyl, or a dialkylcarbamoyl group, such as dimethylcarbamoyl, and in which the amino group in the side-chain is present in acylated form, e.g. as an alkanoylamino group, such as acetylamino or pivaloylamino, as an alkoxycarbonylamino group, such as t-butoxycarbonylamino, can be used. In addition, amino acids in which a carboxy group in the side-chain is present as an arylmethoxycarbonylamino group, such as benzyloxycarbonylamino, can be used. A hydroxy group in the side-chain can be present in a etherified or esterified form, e.g. as an alkoxy group, such as methoxy, and also as an arylalkoxy group, such as benzyloxy, or as a lower-alkanoyloxy group, such as acetoxy. Suitable N-acyl groups are alkanoyl, such as acetyl or pivaloyl, alkoxycarbonyl, such as t-butoxycarbonyl and arylalkoxycarbonyl, such as benzyloxycarbonyl.

Examples of suitable unsubstituted and substituted aliphatic, aromatic and aromatic-aliphatic carboxylic acids, which can optionally be used in the form of their protected derivatives, are propionic acid, isobutyric acid, (R)- and (S)-lactic acid as well as the corresponding racemates, 2-phthalimidoxy-isobutyric acid and benzoic acid, 3,4-dihydroxybenzoic acid, salicylic acid, 1-naphthoic acid, 2-naphthoic acid, phenylacetic acid, p-hydroxyphenyl-acetic acid, (S)-α-[(t-butyl-sulphonyl)methyl] hydrocinnamic acid and (S)-α-[[[1-(morpholinocarbonyl)-1-methylethyl]sulphonyl]methyl]-hydrocinnamic acid. 2-Pyridinecarboxylic acid, 3-pyridinecarboxylic acid, 4-pyridinecarboxylic acid, 5-chloro-2-pyridinecarboxylic acid, 2-pyrimidinecarboxylic acid, 4-pyrimidinecarboxylic acid, 2-quinolinecarboxylic acid, 3-quinolinecarboxylic acid, 2-pyridylacetic acid, 3-indolylacetic acid, 3-(3-indolyl) propionic acid, isoquinoline-1-carboxylic acid and (4-imidazolyl)acetic acid can be named as examples of suitable heteroaromatic or heteroaromatic-aliphatic carboxylic acid.

Examples of suitable aforementioned amino acids, which optionally can be used in the form of their protected derivatives, are glycine, alanine, valine, norvaline, leucine, isoleucine, norleucine, serine, homoserine, threonine, methionine, cysteine, proline, trans-3- and trans-4-hydroxyproline, phenylalanine, tyrosine, 4-nitrophenylalanine, 4-aminophenylalanine, 4-chlorophenylalanine,β-phenylserine, phenylglycine, α-naphthylalanine, cyclohexylalanine, cyclohexyl-glycine, tryryptophan, indoline-2-carboxylic acid, 1,2,3,4-tetrahydroisoquinoline-3-carboxylic acid, aspartic acid, asparagine, aminomalonic acid, aminomalonic acid monoamide, glutamic acid, glutamic acid mono-t-butyl ester, glutamine, N-dimethylglutamine, histidine, arginine, lysine, N-t-butoxycarbonyllysine,δ-hydroxylysine, ornithine, N-pivaloyl-ornithine, α,γ-diaminobutyric acid or α,β-diaminopropionic acid and the like. Corresponding peptides which consist e.g of the aforementioned amino acids are also included.

Preferred carboxylic acids are the quinoline-2-carboxylic acids as well as the protected aminocarboxylic acids of formula I

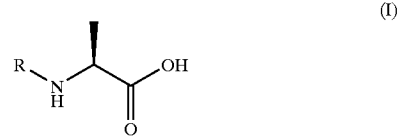

In which R is an amino protecting group. Especially preferred carboxylic acids are quinolinecarboxylic acids as well as acids of formula I in which R represents the benzyloxycarbonyl or tert.-butoxycarbonyl protecting group, for example (S)-2-benzyloxycarbonylamino-propionic acid or (S)-2-tert.-butoxycarbonylamino-propionic acid.

The described acids are commercially available or can be produced by reaction with reactive derivatives of the amino protecting groups.

The term "alkyl" denotes cyclic, branched or straight-chain alkyl groups with 1–8, preferably 1–4, carbon atoms.

The term "aryl" or "aromatic" alone or in combination means the phenyl or naphthyl group which can be optionally mono- or multiply-substituted by alkyl, e.g. methyl, halogen, a protected hydroxy group, alkoxy, e.g. methoxy, alkanoyloxy, e.g. acetoxy, a protected amino or alkylamino group, alkanoylamino, e.g. acetylamino or pivaloylamino, alkoxycarbonylamino, e.g. t-butoxycarbonylamino, arylmethoxycarbonylamino, e.g. benzyloxycarbonylamino or 9-fluorenylmethoxycarbonyl, and/or nitro. Substitution with akyl or halogen is preferred and substitution with alkyl is especially preferred.

The term "cycloalkyl" means cyclic alkyl groups with 3 to 8 C atoms.

The term "halogen" denotes fluorine, chlorine, bromine and iodine.

The term "heteroaryl" refers to an aromatic 5- or 6-membered ring which can contain 1 or 2 atoms selected from nitrogen, oxygen or sulphur and which may have a substitution pattern as described earlier in connection with the term "aryl".

The term "amino protecting group" refers to any protecting group conventionally used to replace an acidic proton of an amino group which can be hydrolyzed to yield the amino group containing the acidic proton. Examples of such groups are described in Green, T., Protective Groups in Organic Synthesis, Chapter 7, John Wiley and Sons, Inc. (1981), pp. 218–287, herein incorporated by reference. The benzyloxycarbonyl and the tert.-butoxycarbonyl protecting groups are examples of such amino protecting groups. Other examples include carbamates, e.g. fluorenylmethyl, 2,2,2-trichloroethyl, 2-haloethyl, 2-(trimethylsilyl)ethyl, t-butyl, allyl, benzyl. Further protecting groups are 3,5-dimethoxybenzyl, p-nitro-benzyl, diphenylmethyl, triphenylmethyl, benzyl, formylj, acetyl, trifluoroacetyl, chloro-acetyl, the cyclic imides of N-phthaloyl, N-trimethylsilyl, N-benzenesulfonyl, N-toluenesulfonyl, N-p-methylbenzyl-sulfonyl.

The term "reactive acid derivatives" means acid halide, acid anhydride or alkyl haloformate derivatives of carboxylic acids. Acid halide derivatives are preferred. The corresponding carboxylic acid chlorides and the corresponding protected aminocarboxylic acid chlorides, for example alkanecarboxylic acid chlorides, are also preferred. Especially preferred are reactive derivatives such as anhydrides or acid halides which are derived from an acid $R^1$—COOH in which $R^1$ is alkyl, cycloalkyl, heteroaryl or aryl. Compounds in which $R^1$ is alkyl or aryl are preferred; compounds in which $R^1$ is alkyl are especially preferred. Thus, the corresponding acid halides ($R^1$—C(O)Hal), especially the chlorides (the acid chlorides $R^1$—C(O)Cl), are preferred. Branched aliphatic carboxylic acid halides, such as e.g. 2-ethylbutyryl chloride, cyclohexanecarboxylic acid chloride, 2,2-dimethyl-propionyl chloride (pivaloyl chloride) and isovaleroyl chloride, are preferably used because of the steric and positive inductive effects. Furthermore, corresponding anhydrides can also be used the process in accordance with the invention. Moreover, alkyl chloroformates, e.g. ethyl chloroformate, can be used. The especially preferred reactive acid derivatives are pivaloyl chloride, isovaleroyl chloride and ethyl chloroformate. The corresponding halides are commercially available or can be produced according to known methods. For example, the corresponding acid chlorides can be produced by reacting the acid with thionyl chloride, phosphorus trichloride or phosphorus pentachloride. Anhydrides can be produced according to the process described in the Application. The aforementioned alkyl chloroformates are commercially available or can be produced according to known methods.

In accordance with this invention any conventional base utilized in anhydride formation reactions can be used in the reaction of this invention. Among the bases which can be utilized are the organic bases such as the tertiary amines (both aliphatic and aromatic), or the alkali and alkaline earth salts of the carboxylic acids used in the respective reaction. Examples of tertiary amines include pyridine, N-alkylmorpholines, e.g. N-methyl- and N-ethylmorpholine, and dialkylanilines, such as dimethylaniline. Triethylamine is preferred. In the case of alkali and alkaline earth salts of the carboxylic acids, the sodium and potassium salts are preferred. The by far most preferred bases are tertiary amines, such as N-ethylmorpholine, dimethylaniline, triethylamine and N,N,N',N'-tetramethylethylenediamine, especially triethylamine.

As used herein the term "pharmaceutically suitable salts" means salts derived from metals, the ammonium salt, quaternary ammonium salts derived from organic bases and amino acid salts. Examples of metal salts are those derived from the alkali metals, for example lithium (Li+), sodium (Na+) and potassium (K+). Examples of quaternary ammonium salts derived from organic bases include tetramethylammonium (N+($CH_3$)$_4$), tetraethylammonium (N+($CH_2CH_3$)$_4$), benzyltrimethylammonium (N+($C_6H_5CH_2$)($CH_3$)$_3$), phenyltriethylammonium (N+($C_6H_5$)($CH_2CH_3$)$_3$), and the like. Those salts derived from amines include salts with N-ethylpiperidine, procaine, dibenzylamine, N,N'-dibenzylethylenediamine, alkylamines or dialkylamines as well as salts with amino acids such as, for example, salts with arginine or lysine. Other examples include hydrochlorides, sulfates, phosphates, lactates, and mesylates.

Any conventional inert solvent can be used as the solvent. Examples of such inert solvents include tetrahydrofuran, toluene, hexane, acetone, dioxan, preferably lower carboxylic acid esters such as alkyl acetates, primarily methyl, ethyl and isopropyl acetate.

Advantageously, the reaction is carried out with temperature control at between −25 and +25° C., preferably between 0 and +5° C.

Anhydrides which can be manufactured according to the process in accordance with the invention are likewise an object of the present invention. Thus, the present invention also embraces anhydrides of the formula

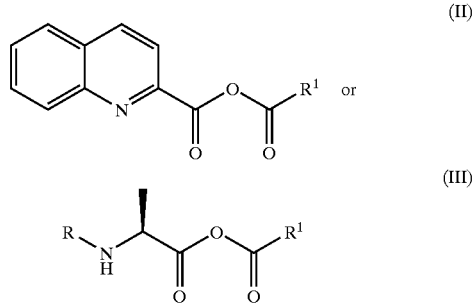

in which R is an amino protecting group and $R^1$ is alkyl, cycloalkyl, heteroaryl or aryl. Compounds in which $R^1$ is alkyl or aryl are preferred; compounds in which $R^1$ is alkyl are especially preferred. (S)-2-Benzyloxycarbonylaminopropionic acid-2,2-dimethyl-propionic acid anhydride, (S)-2-tert.-butoxycarbonylamino-propionic acid-2,2-dimethylpropionic acid-anhydride and 2,2-dimethyl-propionic acid quinoline-2-carboxylic acid anhydride are examples of these compounds.

The process described above is suitable, for example, for use in peptide synthesis and/or for the manufacture of pharmaceutically active substances or corresponding starting materials or intermediates.

Thus, the present invention embraces a process for the manufacture of a mixed quinoline-2-carboxylic acid anhydride of the formula

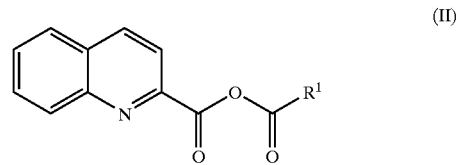

wherein $R^1$ is as defined above, in accordance with the described process. Quinoline-2-carboxylic acid is thereby reacted with the corresponding reactive acid derivative, e.g. an anhydride or preferably an acid halide which is derived from the corresponding acid $R^1$—COOH. The corresponding acid chloride is preferred.

The resulting anhydride of formula II above can then be converted, for example, into N-(2-quinolylcarbonyl)-L-asparagine (quinargine) by reaction with asparagine. Quinargine is known per se and is described, for example, in European Patent Application No. 611774. It is a valuable intermediate for the manufacture of pharmacologically active compounds. Thus, quinargine can be converted as described in Example 7 of the aforementioned European Patent Application into pharmacologically active compounds which are suitable primarily for the treatment of viral infections, especially such infections which are caused by HIV or other retroviruses.

For the manufacture of quinargine according to the process described above, quinoline-2-carboxylic acid can be reacted with a reactive derivative of an acid $R^1$—COOH, in which $R^1$ is defined above, for example with pivaloyl chloride, and an adjuvant base, e.g. triethylamine. This reaction, which is described in detail in Example 1, yields the corresponding mixed anhydride, here e.g. 2,2-dimethylpropionic acid-quinoline-2-carboxylic acid anhydride, which, after isolation or even directly without further purification, can be reacted with asparagine in an aqueous, alkaline solution to give quinargine. The reaction with asparagine preferably takes place in an aqueous NaOH/NaHCO$_3$ solution. With this process N-(2-quinolylcarbonyl)-L-asparagine (S-quinargine) can be manufactured directly from the educts in high yield without the isolation of an intermediate.

Furthermore, the present invention embraces the manufacture of pharmaceutically active substances. For example, the aforementioned N-(2-quinolylcarbonyl)-L-asparagine can be converted by reaction with 2-[3(S)-amino-2(R)-hydroxy-4-phenylbutyl]-N-tert.butyl-decahydro-(4aS,8aS)-isoquinoline-3(S)carboxamide, which is known from European Patent Application No. 635,493, in the presence of a coupling reagent such as e.g. a carbodiimide and a N-hydroxy compound, with the N-hydroxy compound being present in a catalytic amount. As described in Example 7 of European Patent Application No. 611774, the aforementioned substances can be converted in the presence of dicyclohexylcarbodiimide using a catalytic amount of 1-hydroxy-2(1H)-pyridone in an inert solvent or solvent mixture such as ethyl acetate/tetrahydrofuran into N-t-butyl-decahydro-2-[2(R)-hydroxy-4-phenyl-3(S)-[[N-(2-quinolylcarbonyl)-L-asparaginyl]-amino]butyl]-(4aS,8aS)-isoquinoline-3(S)-carboxamide or into pharmaceutically suitable salts or corresponding esters derived therefrom.

Accordingly, the present invention also includes a process for the manufacture of these compounds. Such a process embraces in a first step the manufacture of a mixed anhydride and its conversion into quinargine as described above. The mixed anhydride, e.g. 2,2-dimethylpropionic acid-quinoline-2-carboxylic acid anhydride, can be obtained by adding an adjuvant base, e.g. triethylamine, to a mixture of quinoline-2-carboxylic acid and a reactive acid derivative, preferably pivaloyl chloride. The resulting mixed anhydride is subsequently reacted with asparagine in alkaline solution to give N-(2-quinolylcarbonyl)-L-asparagine. This substance is then converted in a subsequent step with 2-[3(S)-amino-2(R)-hydroxy-4-phenylbutyl]-N-tert.butyl-decahydro-(4aS, 8aS)-isoquinoline-3(S)carboxamide into N-t-butyl-decahydro-2-[2(R)-hydroxy-4-phenyl-3(S)-[[N-(2-quinolylcarbonyl)-L-asparaginyl]-amino]butyl]-(4aS, 8aS)-isoquinoline-3(S)-carboxamide as described above or optionally into a corresponding salt, preferably the methanesulphonic acid salt, or into an ester.

Furthermore, by means of the process in accordance with a invention it is possible to convert an acid of formula I

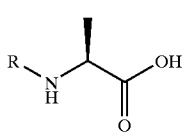

(I)

with a reactive derivative of an acid R$^1$—COOH into an anhydride of formula III

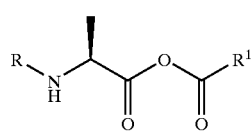

(III)

wherein R is an amino protecting group as defined above and R$^1$ is alkyl, cycloalkyl, heteroaryl or aryl. Preferred processes are those in which compounds are used in which R$^1$ is alkyl or aryl; compounds in which R$^1$ is alkyl are especially preferred. The amino protecting group can be a protecting group known from the state of the art, such as, for example, as used in peptide chemistry. The benzyloxycarbonyl and tert.-butoxycarbonyl protecting groups are examples of such amino protecting groups.

Thus, using the process in accordance with the invention it is possible to manufacture ethyl (S)-[1-(2-benzyloxycarbonylamino-propionyl)-piperidin-4-yloxy]-acetate and ethyl (S)-[1-(2-tert.-butoxycarbonylamino-propionyl)-piperidin-4-yloxy]-acetate, which are also important pharmaceutical intermediates. As described in Examples 2 and 3, the corresponding intermediates can be obtained also in these cases in very good yields even without isolation of the corresponding mixed anhydrides. In particular, the reaction is effected by reacting a protected aminopropionic acid, e.g. (S)-2-benzyloxycarbonylamino-propionic acid or, respectively, (S)-2-tert.-butoxycarbonylamino-propionic acid, with a reactive acid derivative as described above, here in both cases with pivaloyl chloride, using a tertiary amine, here triethylamine, as the adjuvant base. The amino protecting group of the aminopropionic acid can be any suitable amino protecting group, with the benzyloxycarbonyl and tert.-butoxycarbonyl protecting groups being preferred. The resulting mixed anhydrides (S)-2-benzyloxycarbonylaminopropionic acid-2, 2-dimethylpropionic acid anhydride and (S)-2-tert.-butoxycarbonylamino-propionic acid-2,2-dimethylpropionic acid anhydride can be reacted with ethyl (piperidin-4-yloxy)-acetate, e.g. in a potassium phosphate-buffered, aqueous ethyl acetate suspension, to give the aforementioned intermediates. These intermediates can be processed further to give pharmaceutically active substances.

For example, with the process in accordance with the invention it is possible to use these intermediates for the manufacture of ethyl [Z]-(S)-[[1-[2-[[4-(amino-hydroximino-methyl)-benzoyl]amino]-1-oxopropyl]-4-piperidinyl]oxy]acetate, a fibrinogen receptor antagonist (Alig et al. (1992) J. Med. Chem. 35, 4393–4407; Weller et al. (1996) J. Med. Chem. 39, 3139–3147). The process described above can be performed as follows for the manufacture of this substance: The protecting groups can be cleaved off from the aforementioned intermediates and the amine obtained can be converted with a corresponding acid chloride and subsequent reaction with hydroxylamine into the desired substance. In particular, the benzyloxycarbonyl protecting group can be cleaved off by hydrogenation and the tert.-butoxycarbonyl protecting group can be cleaved off by acid from, respectively, ethyl (S)-[1-(2-benzyloxycarbonylamino-propionyl)-piperidin-4-yloxy]-acetate and ethyl (S)-[1-(2-tert.-butoxycarbonylamino-propionyl)-piperidin-4-yloxy]-acetate. The liberated amine can then reacted with 4-cyanobenzoyl chloride, which can be prepared from thionyl chloride and 4-cyanobenzoic acid, and subsequently converted by reaction with hydroxylamine hydrochloride and triethylamine and working-up in acidic medium into ethyl [Z]-(S)-[[1-[2-[[4-(amino-hydroximino-methyl)-benzoyl]amino]-1-oxopropyl]-4-piperidinyl]oxy] acetate in accordance with Example 4.

Accordingly, the process in accordance with the invention also relates to the manufacture of ethyl [Z]-(S)-[[1-[2-[[4-(amino-hydroximino-methyl)-benzoyl]amino]-1-oxopropyl]-4-piperidinyl]oxy]acetate by producing a mixed anhydride in a first step as described above and converting it by reaction with a compound of formula IV

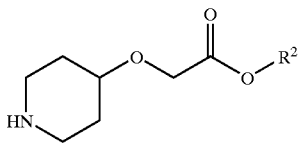

(IV)

wherein R² represents an alkyl group, preferably ethyl or tert.-butyl, into an ester or formula V

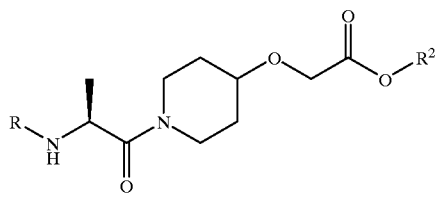

(V)

wherein R and R² are as defined above. Subsequently, the amino protecting group R can be cleaved off and optionally the R² group can be trans-esterified to the ethyl ester, with the cleavage of the amino protecting group and the trans-esterification to the ethyl ester being optionally carried out simultaneously depending on the protecting group used, e.g. in the case of the tert.-butyl protecting group by reaction with $H_2SO_4$/ethanol. Subsequently, the resulting amine of formula VI

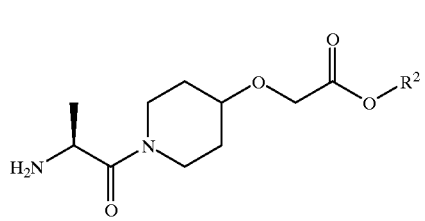

(VI)

wherein R² is as defined above, can be reacted with 4-cyanobenzoyl chloride to give the compound of formula VII

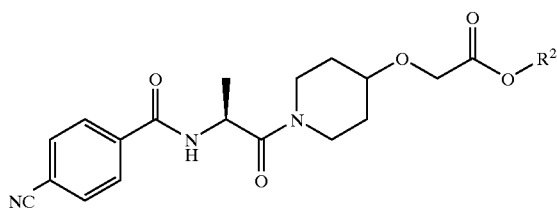

(VII)

wherein R² is as defined above. Alternatively, when e.g. the benzyloxycarbonyl protecting group is used, the cleavage of the protecting group can be effected by hydrogenation, followed by reaction with 4-cyanobenzoyl chloride and transesterification to the corresponding ethyl ester (R²= ethyl). Of course, the corresponding ethyl ester may be introduced simultaneously as described in Example 4 via compound IV with R²=ethyl. Subsequently, ethyl [Z]-(S)-[[1-[2-[[4-(amino-hydroxyimino-methyl)-benzoyl]amino]-1-oxopropyl]-4-piperidinyl]oxy]acetate can be obtained by reacting hydroxylamine hydrochloride with the compound of formula VII. If desired, the compound obtained can be converted into a pharmaceutically suitable salt.

The following Examples illustrate the invention and do not have any limiting character.

EXAMPLES

Example 1

Manufacture of N-(2-quinolylcarbonyl)-L-asparagine (S-quinargine)

34.60 g (200 mmol) of quinoline-2-carboxylic acid (Benechim S. A.) were suspended in 350 ml of ethyl acetate (Fluka) while stirring and under a protective gas at 0 to 5° C. and treated with 25.0 ml (200 mmol) of pivaloyl chloride (Fluka). 28.0 ml (200 mmol) of triethylamine (Fluka) were added to the white suspension within 30 minutes, with the temperature being held at 0 to 5° C. Subsequently, the suspension was stirred at 0 to 5° C. for 30 minutes. The white suspension was filtered and the filter cake was washed with 100 ml of cooled (0–5° C.) ethyl acetate (Fluka). The filtrate contained the resulting 2,2-dimethylpropionic acid-quinoline-2-carboxylic acid anhydride having the following characteristics: melting point: 47° C.; MS: [M+H]⁺258; IR: 1750 cm⁻¹, 1775 cm⁻¹. The cooled (0—5° C.), light yellow filtrates were combined and treated within 5 minutes while stirring intensively with a pre-cooled solution of 30.0 g (200 mmol) of L-asparagine (Fluka), 8.0 g (200 mmol) of sodium hydroxide (Fluka) and 16.80 g (200 mmol) of sodium bicarbonate in 350 ml of cold, deionised water (0–5° C.), with the temperature being held at between 0 and 5° C. Subsequently, the cooling was removed and the light green two-phase system was stirred at room temperature for about 17 hours. The aqueous phase of the now colourless two-phase system was treated with 200 ml of methanol (Merck) while stirring and under argon. Then, 49 ml of 25% hydrochloric acid (Merck) were added dropwise to pH 3.0. In so doing, the temperature rose to 28° C. and crystallization set in. The white suspension was stirred at room temperature for one hour, subsequently cooled to 0–5° C. and stirred at this temperature for a further hour. The filtered-off filter cake was washed with a total of 80 ml of cold, deionised water (0–5° C.) and dried in a rotary evaporator at 5° C./10 mbar for 6 hours. Yield: 47.52 g (83%) of N-(2-quinolylcarbonyl)-L-asparagine in the form of white crystals [melting point: 209° C. (decomposition), HPLC analysis 99.8% (area)].

Example 2

Manufacture of ethyl (S)-[1-2-2 (benzyloxycarbonylaminopropionyl)-piperidin-4-yloxy]-acetate 55.8 g (250 mmol) of (S)-2-benzyloxycarbonylamino-propionic acid (obtainable from the corresponding aminocarboxylic acid by protection of the amino function with a benzyloxycarbonyl derivative; Bodansky et al., loc. cit.) were dissolved in 560 ml of ethyl acetate (Fluka) while stirring and under argon, cooled to 0 to 5° C. and treated with 31.0 ml (250 mmol) of pivaloyl chloride (Fluka). 35.0 ml of triethylamine (Fluka) were added dropwise to the light yellowish solution within 30 minutes, with the temperature being held at 0 to 5° C. A white suspension formed. The white precipitate was filtered off through a pre-cooled glass filter (G3) and the filter cake was washed with 140 ml of cold ethyl acetate (0 to 5° C., Fluka). To the combined filtrates, a clear, colourless liquid which contained the anhydride, were added 55.9 g (250 mmol) of ethyl (piperidin-4-yloxy)-acetate hydrochloride (obtainable from the corresponding tert.-butyl compound (Alig et al., loc. cit.) by transesterification with ethanol/hydrochloric acid) and 66.6 g (250 mmol) of Na$_3$PO$_4$.3H$_2$O. The white suspension was treated at 5 to 10° C. 500 ml of deionised water within 30 seconds under argon and while stirring vigorously, with the temperature rising to 20° C. The colourless two-phase system was stirred vigorously at 20 to 25° C. for one hour. Subsequently, the aqueous phase was separated and the organic phase was washed with 1M sodium bicarbonate solution and then with 1N aqueous ammonia solution. The organic phase was dried over about 50 g of sodium sulphate, filtered and the filter cake was washed with about 100 ml of ethyl acetate. The combined filtrates were evaporated in a rotary evaporator and the oily residue was taken up with 100 ml of ethanol. The clear solution was evaporated at 50°/20 mbar to give 90.2 g (92 wt. %) of ethyl (S)-[1-(2-benzyloxycarbonylaminopropionyl)-piperidin-4-yloxy]-acetate as a clear, colourless oil.

Example 3

Manufacture of(S)-[1-(2-tert.-butoxycarbonylaminopropionyl)-piperidin-4-yloxy]-acetate 47.3 g (250 mmol) of (S)-2-tert.-butoxycarbonyl- amino-propionic acid (Fluka) were dissolved in 560 ml of ethyl acetate (Fluka) while stirring and under argon, cooled to 0–5° C. and treated with 31.0 ml (250 mmol) of pivaloyl chloride (d=98; Fluka). The light yellowish solution was treated dropwise within 30 minutes with 35.0 ml (250 mmol) of triethylamine (d=0.726; Fluka), with the temperature being held in the range of 0–5° C. A white suspension formed. The white precipitate was filtered off through a pre-cooled, sintered glass filter (G3) and the filter cake was washed with 140 ml of cold ethyl acetate (0 to 5° C.). To the combined filtrates, a light yellow solution, were added 55.9 g (17.HCl; 250 mmol) of ethyl (piperidin-4-yloxy)-acetate hydrochloride and 66.6 g of K$_3$PO$_4$.3H$_2$O (250 mmol; Merck). The white suspension was treated with 500 ml of deionised water at 5 to 10° C. under argon and while stirring vigorously, with the temperature rising to 20° C. The colourless two-phase system was stirred at 20 to 25° C. for two hours. The aqueous phase was separated and the organic phase was washed with 500 ml of a 1M sodium bicarbonate solution. The organic phase was dried over about 50 g of sodium sulphate, filtered and the filter cake was washed with about 100 ml of ethyl acetate. The combined filtrates were evaporated in a rotary evaporator at 50°/20 mbar, giving 85.5 g (95 wt. %) of ethyl (S)-[1-(2-tert.-butoxycarbonylamino-propionyl)-piperidin-4-yloxy]-acetate as a crude product in the form of a clear, yellowish oil (HPLC analysis: 88.9% (area).

Example 4

Manufacture of ethyl [Z]-(S)-[[1-[2-[[4-(amino-hydroximino-methyl)-benzoyl]amino]-1-oxopropyl]-4-piperidinyloxy]-acetate For the manufacture of the aforementioned compound, 90.2 g (230 mmol) of ethyl (S)-[1-(2-benzyloxycarbonyl-amino-propionyl)-piperidin-4-yloxy]-acetate in 450 ml of ethanol were treated with 4.5 g of 10% palladium/charcoal and the resulting solution was hydrogenated while stirring intensively at a hydrogen pressure of 1.1 bar at 22 to 24° C. for 40 minutes. After evacuation the hydrogenation kettle was again filled and stirred for a further 30 minutes. The suspension was subsequently filtered over 30 g of Speedex (Dicalite Speedex), the filter cake obtained was washed with 450 ml of ethanol and the combined, clear filtrates were cooled to 0 to 5° C. and treated with 32 ml (230 mmol) of triethylamine (230 mmol). To this solution was added while stirring a light yellow solution of 38 g (230 mmol) of 4-cyanobenzoyl chloride in 80 ml of toluene, with the temperature being held at between 0 and 5° C. The light yellow solution was stirred at room temperature for one hour and then treated with 31.9 g (460 mmol) of hydroxylamine hydrochloride (Fluka) and with 64 ml (460 mmol) of tri-ethylamine (Fluka), with the temperature rising to about 28° C. The white suspension was stirred at room temperature (20 to 25° C.) for 17 hours, with an almost clear suspension forming after one hour and a white precipitate forming thereafter. The white suspension was treated with 36 ml of 25% hydrochloric acid. The suspension was cooled to 0 to 5° C., stirred for one hour, filtered through a pre-cooled sintered glass filter (G3) and the filter cake was washed with 250 ml of cold ethanol. Subsequently, it was dried to constant weight, giving 70.6 g (73 wt. %) of ethyl [Z]-(S)-[[1-[2-[[4-(amino-hydroximino-methyl)-benzoyl]amino]-1-oxopropyl]-4-piperidinyl]oxy]acetate. The powder was dissolved in a mixture of 560 ml of ethanol and 140 ml of water under reflux and while stirring and subsequently the solution was cooled to room temperature within two hours and then stirred at a temperature of 0 to 5° C. for one hour. The solution was filtered through a pre-cooled glass filter (G3) and the filter cake was washed with a mixture of 140 ml of cold ethanol (0 to 5° C.) and 35 ml of cold water (0 to 5° C.); the product was subsequently dried to constant weight at 50° C./20 mbar. The resulting white crystals (65.6 g; 68 wt. %) were suspended in a mixture of 528 ml of ethanol and 132 ml of water and treated with 3.3 g of active charcoal (Norit SX-1). The dark suspension was heated under reflux for 15 minutes, cooled to 65 to 70° C. and added via a glass filter to a pre-warmed funnel. The filtrates were stirred, with a precipitate separating from 60° C. The white suspension was cooled to room temperature within three hours, then cooled to 0 to 5° C. and, after stirring for one hour, filtered through a correspondingly pre-cooled sintered glass filter (G3). The filter cake was washed with a mixture of 132 ml of cold ethanol and 33 ml of water (0 to 5° C.) and subsequently dried to constant weight at 50° C./20 mbar. Yield: 60.15 g (55%); m.p.: 212–213°; ee (HPLC)>99.9%; opt. rot. [α]$_{365}$+ 223.5 (c =1.0; HCl).

Example 5

Manufacture of additional mixed anhydrides

Additional compounds can be manufactured according to the process in accordance with the invention analogously to Examples 1 to 3. The results of further reactions are compiled in the following Table.

| Educt 1 | Educt 2 | Anhydride | Coupling product |
|---|---|---|---|
| quinoline-2-COOH, 17.32 g | pivaloyl chloride, 12.1 g | quinoline-2-carboxylic pivalic anhydride, IR: 1775, 1755 cm$^{-1}$ | quinoline-2-CO-NH-CH(CH$_2$CONH$_2$)-COOH, 25.73 g (90%) |
| quinoline-2-COOH, 1.73 g | CH$_3$SO$_2$Cl, 1.15 g | quinoline-2-carboxylic methanesulfonic anhydride, IR: 1782, 1739 cm$^{-1}$ | quinoline-2-CO-NH-CH(CH$_2$CONH$_2$)-COOH, 1.53 g (53%) |
| quinoline-2-COOH, 1.73 g | isobutyryl chloride, 1.06 g | quinoline-2-carboxylic isobutyric anhydride, IR: 1808, 1753 cm$^{-1}$ | quinoline-2-CO-NH-CH(CH$_2$CONH$_2$)-COOH, 1.59 g (61%) |

| Educt 1 | Educt 2 | Anhydride | Coupling product |
|---|---|---|---|
| quinoline-2-COOH, 1.73 g | isobutyl-CH2-COCl, 1.20 g | quinoline-2-C(O)-O-C(O)-CH2-CH(CH3)2, IR: 1812, 1756 cm$^{-1}$ | quinoline-2-C(O)-NH-CH(COOH)-CH2-CONH2, 2.14 g (75%) |
| quinoline-2-COOH, 1.73 g | (Et)2CH-COCl, 1.35 g | quinoline-2-C(O)-O-C(O)-CH(Et)2, IR: 1805, 1749 cm$^{-1}$ | quinoline-2-C(O)-NH-CH(COOH)-CH2-CONH2, 2.0 g (74%) |
| quinoline-2-COOH, 1.73 g | cyclohexyl-COCl, 1.47 g | quinoline-2-C(O)-O-C(O)-cyclohexyl, IR: 1807, 1753 cm$^{-1}$ | quinoline-2-C(O)-NH-CH(COOH)-CH2-CONH2, 2.14 g (83%) |

-continued

| Educt 1 | Educt 2 | Anhydride | Coupling product |
|---|---|---|---|
| quinoline-2-COOH, 1.73 g | 2-ethylhexanoyl chloride, 1.63 g | mixed anhydride (quinoline-2-CO-O-CO-CH(Et)Bu), IR: 1804, 1750 cm$^{-1}$ | quinoline-2-CO-NH-CH(COOH)-CH$_2$-CONH$_2$, 2.2 g (77%) |
| quinoline-2-COOH, 1.73 g | benzoyl chloride, 1.41 g | mixed anhydride (quinoline-2-CO-O-CO-Ph), IR: 1795, 1731 cm$^{-1}$ | quinoline-2-CO-NH-CH(COOH)-CH$_2$-CONH$_2$, 2.31 g (81%) |
| quinoline-2-COOH, 1.73 g | 2,4,6-trimethylbenzoyl chloride, 1.83 g | mixed anhydride (quinoline-2-CO-O-CO-Mes), IR: 1787, 1731 cm$^{-1}$ | |
| quinoline-2-COOH, 1.73 g | ethyl chloroformate, 1.08 g | mixed anhydride (quinoline-2-CO-O-CO-OEt), IR: 1790, 1735 cm$^{-1}$ | quinoline-2-CO-NH-CH(COOH)-CH$_2$-CONH$_2$, 1.64 g (57%) |

| Educt 1 | Educt 2 | Anhydride | Coupling product |
|---|---|---|---|
| Cbz-Ala-OH 55.8 g | Pivaloyl chloride 30.14 g | Mixed anhydride IR: 1817, 1750 cm$^{-1}$ | Cbz-Ala-piperidinyl-O-CH$_2$-CO$_2$Et 90.20 g (92%) |
| Boc-Ala-OH 47.3 g | Pivaloyl chloride 30.14 g | Mixed anhydride IR: 1817, 1748 cm$^{-1}$ | Boc-Ala-piperidinyl-O-CH$_2$-CO$_2$Et 85.50 g (95%) |

What is claimed is:
1. A compound of the formula:
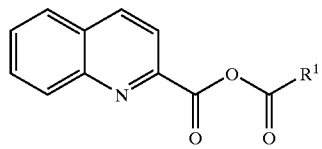
(II)
wherein $R^1$ is selected from the group consisting of t-butyl, isopropyl, isobutyl, 1-ethylpropyl, cyclohexyl, 1-ethylpentyl, phenyl, 2,4,6-trimethylphenyl, and ethoxy.
2. The compound of claim 1, wherein the compound is 2,2-dimethylpropionic acid-quinoline-2-carboxylic acid anhydride.
* * * * *